(12) United States Patent
Chen et al.

(10) Patent No.: US 9,042,973 B2
(45) Date of Patent: May 26, 2015

(54) APPARATUS AND METHOD FOR MEASURING PHYSIOLOGICAL SIGNAL QUALITY

(75) Inventors: Yu Chen, Andover, MA (US); Zhe Zhang, Westford, MA (US)

(73) Assignee: Draeger Medical Systems, Inc., Telford, PA (US)

( * ) Notice: Subject to any disclaimer, the term of this patent is extended or adjusted under 35 U.S.C. 154(b) by 0 days.

(21) Appl. No.: 14/002,870

(22) PCT Filed: Mar. 22, 2012

(86) PCT No.: PCT/US2012/030134
§ 371 (c)(1),
(2), (4) Date: Sep. 3, 2013

(87) PCT Pub. No.: WO2012/129413
PCT Pub. Date: Sep. 27, 2012

(65) Prior Publication Data
US 2013/0338519 A1    Dec. 19, 2013

Related U.S. Application Data

(60) Provisional application No. 61/467,062, filed on Mar. 24, 2011.

(51) Int. Cl.
*A61B 5/04* (2006.01)
*A61B 5/0456* (2006.01)
(Continued)

(52) U.S. Cl.
CPC ............ *A61B 5/0456* (2013.01); *A61B 5/0452* (2013.01); *A61B 5/7221* (2013.01); *A61B 5/0472* (2013.01); *A61B 5/04012* (2013.01)

(58) Field of Classification Search
CPC .................................................. A61B 5/0452

USPC .................................. 600/511, 521; 607/4, 5
See application file for complete search history.

(56) References Cited

U.S. PATENT DOCUMENTS 5,697,378 A    12/1997  Elghazzawi
5,967,994 A    10/1999  Wang
(Continued)

FOREIGN PATENT DOCUMENTS

CN         1859869 A    11/2006
CN       101138493 A     3/2008

OTHER PUBLICATIONS

Farrell, RM and Young, BJ. "Effect of Lead Quality on Computerized ECG Interpretation." *Computers in Cardiology 2004*; 31:173-176. IEEE (2004).
(Continued)

*Primary Examiner* — Amanda Patton
*Assistant Examiner* — Nadia A Mahmood
(74) *Attorney, Agent, or Firm* — Mintz Levin Cohn Ferris Glovsky and Popeo, P.C.

(57) ABSTRACT

An apparatus and method for determining a signal quality of an input signal representing a repetitious phenomena derived from at least one sensor connected to a patient is provided. A detector receives the input signal and determines data representing the repetitious phenomena from the input signal for use in determining at least one patient parameter. A measurement processor is electrically coupled to the detector that determines a first signal quality value by identifying at least one feature of the repetitious phenomena data and compares the at least one feature of a first set of the determined repetitious phenomena data with a second set of the determined repetitious phenomena data to determine a feature variability value and using the feature variability value to determine a stability value representative of the quality of the input signal.

22 Claims, 10 Drawing Sheets

(51) Int. Cl.
  *A61B 5/0452* (2006.01)
  *A61B 5/00* (2006.01)
  *A61B 5/0472* (2006.01)

(56) References Cited

U.S. PATENT DOCUMENTS

| | | | |
|---|---|---|---|
| 2005/0267376 A1* | 12/2005 | Marossero et al. | 600/511 |
| 2006/0167368 A1 | 7/2006 | Sarkela | |
| 2007/0100220 A1 | 5/2007 | Baker | |
| 2010/0023073 A1* | 1/2010 | Belk et al. | 607/4 |
| 2010/0023082 A1 | 1/2010 | Dong et al. | |
| 2011/0316704 A1 | 12/2011 | Nielsen et al. | |

OTHER PUBLICATIONS

Kaiser, Willi and Findeis, Martin. "Artifact Processing During Exercise Testing." *Journal of Electrocardiology*. vol. 32. Supplement 1999:212-219.

Stolojescu, Cristina. "Estimation of Noise in ECG Signals using Wavelets." *11th International Conference on Optimization of Electrical and Electronic Equipment*. May 22-24, 2008: 113-118.

Wang, JY. "A New Method for Evaluating ECG Signal Quality for Multi-Lead Arrhythmia Analysis." *Computers in Cardiology 2002*; 29;85-88. IEEE (2002).

* cited by examiner

APPARATUS AND METHOD FOR MEASURING PHYSIOLOGICAL SIGNAL QUALITY

CROSS-REFERENCE TO RELATED APPLICATIONS

This application is a national stage application, filed under 35 U.S.C. §371, of and claims priority to International Application No.: PCT/US2012/030134, filed on Mar. 22, 2012, which in turn claims priority to U.S. Provisional Pat. App. Ser. No. 61/467,062, filed on Mar. 24, 2011.

FIELD OF THE INVENTION

This invention concerns a system and method for patient monitoring and, more specifically, obtaining a quality measurement of a physiological signal for use in determining and monitoring at least one patient parameter.

BACKGROUND OF THE INVENTION

When providing healthcare to patients it is frequently important to accurately monitor at least one type of patient parameter associated with the patient. To accomplish this, at least one sensor is connected to a patient for use in sensing physiological signals that are provided to and interpreted by at least one type of patient monitoring device. The sensed physiological signals are used in determining the at least one patient parameter. Sensed signals having poor quality negatively impact the ability of the patient monitoring device to determine the desired patient parameter resulting in potentially inaccurate patient parameter data values. Inaccurate patient parameter data may, at best, reduce the efficiency and competency of the healthcare being provided to the patient and, at worst, may result in harm to the patient. Thus, a need exists to provide a system and method for measuring the quality of a physiological signal that is used in determining and monitoring at least one patient parameter.

An example of a sensed physiological signal is electrocardiogram (ECG) signals that represent a series of heartbeats. ECG data of poor quality presents challenges to accurate interpretation in patient monitoring. Recently, it has become commonplace to use multiple ECG leads as inputs to a multi-lead algorithm for detecting arrhythmia in real-time. The key component in the multi-lead algorithm is determining which ECG leads connected to the patient should be included as inputs and subsequently processed by the ECG monitor. By using leads with inferior quality, the performance of the algorithm will be degraded resulting in inaccurate patient parameter data. Therefore, it is desirable to develop a method of measuring the quality of the ECG signals derived from respective leads connected to the patient to identify and select which leads to be used in determining ECG data for the patient.

Clinical experience with current ECG-based monitoring has shown that the best performance can be achieved if the input signal derived from the patient connected sensors is free from noise as noise has been the primary source of performance degradation for multi-lead algorithms as described above. Noise appearing on the ECG may be due to physiologic or non-physiologic sources. The most common noise may be caused by skeletal muscle tremor, electrical interference and electrode movements. Failure to minimize and recognize artifacts in the input signal that are caused by noise during monitoring may result in incorrect detection of heart rate and arrhythmias leading to false alarms and unnecessary clinician intervention.

Invariably, estimation of noise presence in an ECG input signal will result in the ECG algorithm rejecting part or all of the ECG signal. Alternatively, noise estimation may result in allowing the sensed data to proceed for further analysis taking into account the magnitude of the noise present in the ECG. There are a few techniques detecting individual types of noise (mostly, only for high frequency noise, baseline wander, and low frequency noise). Current methods for the detection and/or quantification of composite noise in ECG signals require the accurate QRS detection for individual leads or one combined lead. For example, the classic method to quantify signal quality of each lead, is to represent ECG signal (QRS, P, T) morphology on a template (aligned averaged signal) or model (KLT functions, wavelets, etc), and define the difference between the signal and the representation as the underlying noise in the ECG. There are also some variations in noise definition which propose using a noise index of the T-P interval average power divided by the QRS average power.

However, a drawback associated with the current ECG processing is that reliable QRS detection is not always achievable if the ECG signal is poor due to the inability to distinguish between desired signal data and noise. It is therefore desirable to measure ECG signal quality and determine weighting factors for use in selecting different leads from a set of leads in order to accurately perform QRS detection for a particular patient. A system according to invention principles addresses deficiencies of known systems.

SUMMARY OF THE INVENTION

In one embodiment, an apparatus for determining a signal quality of an input signal representing a repetitious phenomena derived from at least one sensor connected to a patient is provided. A detector receives the input signal and determines data representing the repetitious phenomena from the input signal for use in determining at least one patient parameter. A measurement processor is electrically coupled to the detector that determines a first signal quality value by identifying at least one feature of the repetitious phenomena data and compares the at least one feature of a first set of the determined repetitious phenomena data with a second set of the determined repetitious phenomena data to determine a feature variability value and using the feature variability value to determine a stability value representative of the quality of the input signal.

In another embodiment, a method of determining a signal quality of an input signal representing a repetitious phenomena derived from at least one sensor connected to a patient is provided. The method includes receiving, by a detector, the input signal and determining data representing the repetitious phenomena from the input signal for use in determining at least one patient parameter. A measurement processor electrically coupled to the detector determines a first signal quality value by identifying at least one feature of the repetitious phenomena data, comparing the at least one feature of a first set of the determined repetitious phenomena data with a second set of the determined repetitious phenomena data to determine a feature variability value, and using the feature variability value to determine a stability value representative of the quality of the input signal.

DETAILED DESCRIPTION

Figure 1:
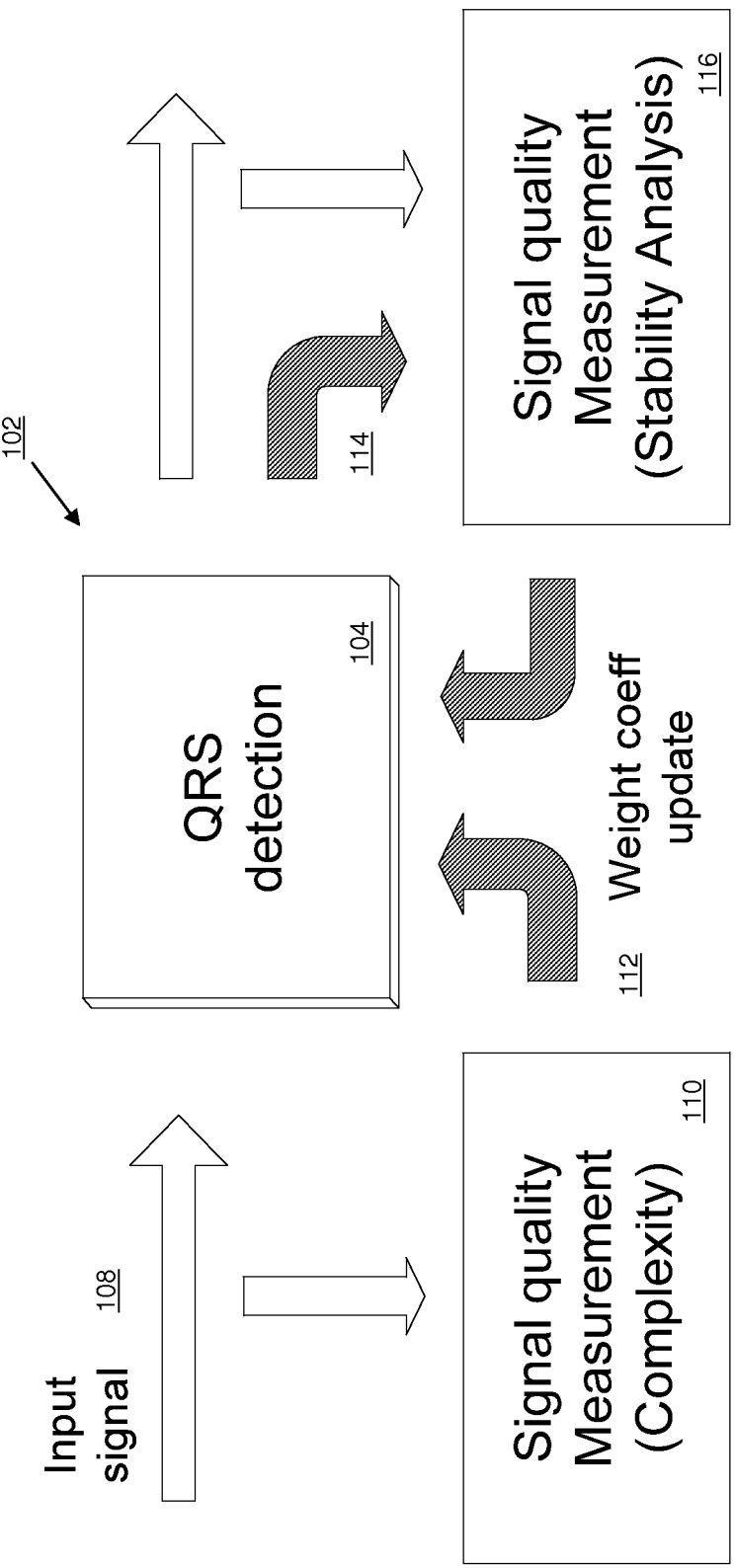
FIG. 1 is a diagram detailing an exemplary process for determining a signal quality measurement for use in multi-lead QRS detection according to invention principles.

A patient monitoring device includes a signal quality measurement system that advantageously measures the quality of a physiological signal being sensed by at least one sensor connected to a patient. The signal quality measurement is advantageously performed on each sensor connected to a patient that senses physiological data from the patient. The system may employ at least one signal quality measurement for use in determining if the signal quality meets a predetermined threshold and therefore may be used by a patient monitoring device in order to determine and monitor at least one patient parameter.

In one embodiment, a first signal quality measurement is associated with a stability measurement of the input signal sensed by a particular sensor. In this embodiment, the stability measurement advantageously identifies at least one feature of the input signal for use in comparing a characteristic of the at least one feature between data samples in a period of previously sensed input signals to determine a quality measurement based on the characteristic differences between samples over the period. If the stability measurement is within a predetermined range, the input signal is designated as being stable and the system identifies that the signal derived from the particular sensor may be used in determining and monitoring the at least one patient parameter. If the stability measurement is outside the predetermined range, the system determines that there is noise on the input signal. By designating a signal as stable, the signal from the particular sensor is determined to be of sufficient quality and able to be selected for use in determining and monitoring the patient parameter data. If the stability measurement determines that the input signal is noisy, the input signal is prevented from being used by the patient monitoring device to determine and monitor the at least one patient parameter. In this embodiment, the stability measurement is performed on data obtained from the input signal sensed by each sensor connected to the patient. The resulting stability measurement advantageously and automatically determines which sensors should be selected to provide data for use in determining and monitoring at least one patient parameter.

In another embodiment, a second signal quality measurement is associated with a complexity measurement of the input signal sensed by a particular sensor. The second signal quality measurement is performed on incoming signals sensed by the particular sensor prior to being processed by the patient monitoring device. In this embodiment, a pre-processor receives input signals from each of the patient connected sensors and determines a complexity measurement for each of the input signals. The complexity measurement is determined automatically and in real-time using a complexity algorithm. The resulting complexity measurement is compared to a threshold which, if exceeded, identifies the signal as noisy and removes it from being considered in determining and monitoring at least one patient parameter.

In a further embodiment, the signal quality measurement system employs both the first signal quality measurement and the second signal quality measurement. This advantageously enables the patient monitoring device to selectively measure the signal quality both in real-time to identify noise prior to processing as well as on a set of processed input signals in order to determine if the processed signals are sufficiently noise-free to ensure a high quality signal for use in determining and monitoring at least one patient parameter. In this embodiment, the first and second signal quality measurements are advantageously assigned a numerical weight that selectively determines which of the input signals are used to determine and monitor the at least one patient parameter.

An ECG monitor is an exemplary patient monitoring device that may selectively implement the signal quality measurement system according to invention principles. In an ECG monitoring setup, at least one electrode (sensor) is connected to predetermined locations on the patient's body. The point of connection of various electrodes is well known in the art and need not be discussed in further detail. The electrodes sense physiological signals from the patient in order to generate data representing ECG leads from the electrodes. ECG lead data is processed to generate an ECG waveform and may be used to detect at least one type of cardiac condition such as an arrhythmia. As noted above, noise on any of the input signals may negatively impact the generated ECG data resulting in false positive indications of the cardiac condition. The signal quality measurement advantageously reduces false positive indications of cardiac conditions by ensuring that the input signals used to determine and detect the cardiac condition are of the highest quality. Thus, the signal quality measurement may be used in identifying which of the respective ECG leads are of high quality and should be selected for processing. Additionally, the signal quality measurement could also be used in determining a weight associated therewith which may be used by a signal processing algorithm to generate the QRS complex.

The first signal quality measurement represents a stability analysis of QRS complex features. In this manner, a stability level of features between continuous small groups of QRS complexes are used together as a scalar of the ECG signal quality such that a high degree of feature variation between the individual QRS complexes in the small group of QRS complexes is indicative of high noise and thus a poor quality signal. The stability measurement advantageously enables the QRS detector to selectively choose the respective source of data for use in calculating subsequent QRS complexes. In the second signal quality measurement, a complexity of the input signal is measured by evaluating the randomness of finite sequences to identify the presence of noise in the signal and determine whether or not that input signal should be used in determining the QRS complexes for the patient. Thus, the QRS detection performance in automated ECG monitoring is dependent on the noise measurement of individual lead and signal quality measurements based on the signal complexity and the stability analysis of QRS complex features advantageously improves individual ECG lead quality assessment.

FIG. 1 is an exemplary block diagram detailing the workflow of the signal quality measurement system embodied in an ECG monitoring device. While the workflow is described for measuring the signal quality of an ECG input signal, it should be understood that the measurement methods described below may be implemented in any patient monitoring device that senses and processes patient physiological signals using patient connected sensors. Other examples of patient monitoring devices that may employ the signal quality measurement system may include an electroencephalographic (EEG) monitoring device.

As shown in FIG. 1 an ECG monitor 102 includes a QRS detector 104 for automatically determining QRS complexes associated with a patient from at least one input signal 108 received thereby. As is well known in the art, the input signal 108 may include a plurality of input signals sensed from a plurality of sensors connected to a patient in a known manner and known configuration. The following description of system workflow will be described with respect to a single input signal but one skilled in the art will recognize that the workflow principles should be applicable to respective input signals sensed by respective sensors connected to the patient.

The input signal 108 by the ECG monitor 102 is simultaneously provided to a pre-processer 110 and to the QRS detector 104. The pre-processor 110 may be a complexity processor that implements an algorithm that automatically measures the signal quality of the input signal 108 by determining a complexity value. An input signal having a high complexity value is determined to include noise that may negatively impact the QRS complex determination if that input signal 108 were to be used by the QRS detector 104. In the event that the input signal 108 is determined to have a high noise level associated therewith, the pre-processor 110 may operate in one of two modes. In a first mode, the pre-processor 110 may signal the QRS detector 104 to ignore the input signal 108 when determining the QRS complex thereby ensuring that input signals 108 of insufficient quality are not processed by the QRS detector 104. This advantageously prevents input signals 108 having poor signal quality from being used to determine and/or monitor the particular patient parameter (e.g. an ECG waveform used to identify an arrhythmia). In a second mode of operation, the pre-processor 110 may automatically assign a numerical weight associated with the complexity of the input signal 108 in the form of a complexity coefficient 112. The complexity coefficient 112 may be provided to the QRS detector 104 and used to determine how much weight a multi-lead QRS algorithm gives to the particular input signal 108 when determining the QRS complex for the particular patient. For example, data in an input signal 108 having a high complexity coefficient indicating a high level of noise may not be used by the multi-lead QRS detection algorithm. The complexity determination made by the pre-processor 110 occurs in real-time as the signal is being received from the sensor and prior to being processed by the QRS detector 104. This advantageously provides a first filter to ensure that the QRS detector 104 is using input signals 108 having the highest quality.

The input signal 108 is automatically received by the QRS detector 104 simultaneously with the pre-processor 110 irrespective of any noise present on the signal. Similarly as described above, the input signal 108 may include a plurality of different input signals derived from any number of patient connected sensors. The following operation will also be described with respect to a single input signal but one skilled in the art will readily understand that this operation may be applied to any input signal 108 concurrently sensed by a patient connected sensor for processing by the QRS detector 104. The QRS detector 104 automatically processes the input signal 108 in a known manner to generate a plurality of sequential QRS complexes using the data contained in the input signal 108. Data representing a set of QRS complexes 114 comprising a predetermined number of previously detected QRS complexes over a predetermined period may be provided to a stability processor 116. The stability processor 116 automatically determines a feature of each QRS complex within the predetermined period for use as a comparison point. The stability processor 116 automatically compares the determined feature for each QRS complex in the predetermined period by applying a statistical analysis thereto. This advantageously identifies differences in the morphology of the determined feature between respective QRS complexes (e.g. heartbeats) during the period in order to determine if there is an unacceptable level of noise present. The differences in feature morphology are averaged over the predetermined period and compared to a stability threshold. In one embodiment, should the stability measurement be indicative of a noisy signal, the stability processor 116 may signal the QRS detector to remove the input signal on the particular lead from being used as part of the multi-lead QRS detection algorithm. In another embodiment, the stability processor 116 may assign a stability coefficient corresponding to the amount of noise detected in the input signal 108. The stability coefficient may be provided to the QRS detector 104 and used to weight the input signal 108 used in calculating the QRS complex. In one example, if there is a high stability coefficient indicating that the signal is stable and has low noise value, the input signal 108 may be weighted heavily so that the QRS detector 104 is sure to use the data in the respective input signal 108 when determining subsequent QRS complexes. If the stability coefficient is low indicating that there are wide variations of the detected feature, the input signal can be weighted at a low level.

In another embodiment, the workflow shown in FIG. 1 may be used collectively such that the complexity coefficient and stability coefficient for each respective input signal 108 are provided to and used by the QRS detector 104 to selectively choose which of the respective input signals are of the highest quality and thus most desirable for use as inputs to the multi-lead QRS detection algorithm implemented by the QRS detector. A signal is determined to be high quality when the input signal 10 has a low complexity and a high stability.

Figure 2:
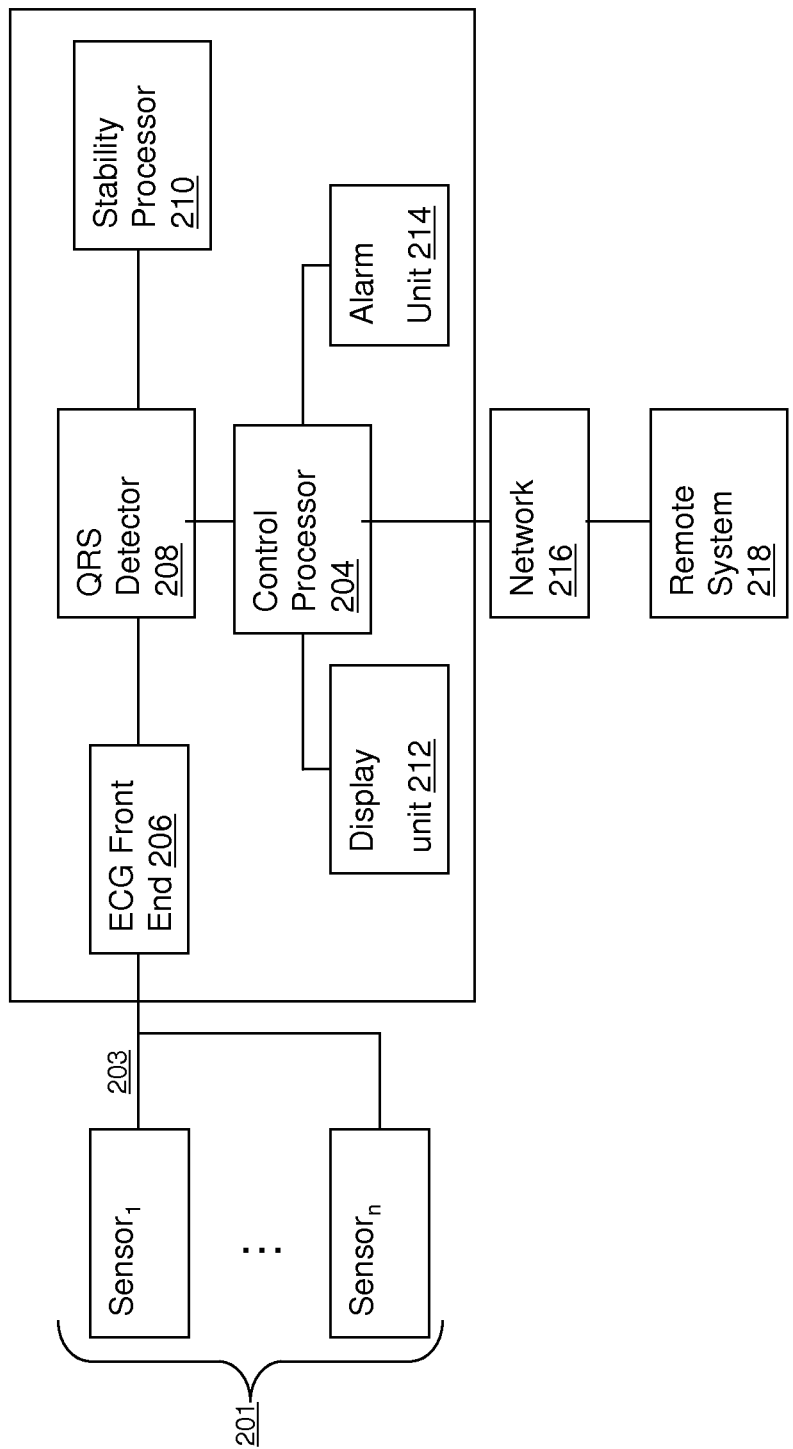
FIG. 2 is a block diagram of an ECG monitor including the a first embodiment of a signal quality measurement system according to invention principles.

FIG. 2 is a block diagram of an exemplary embodiment of the signal quality measurement system according to invention principles. FIG. 2 includes a patient monitoring device 202 having at least one sensor 201 connected thereto. The at least one sensor 201 may be connected to a particular location on the body of a patient for use in sensing data corresponding to a repetitious phenomena exhibited by the patient. The at least one sensor 201 senses a particular type of repetitious phenomena from the patient which is used as an input signal 203 by the patient monitoring device 202. The patient monitoring device 202 includes a control processor 204 that selectively controls the operation thereof. The control processor 204 executes at least one type of monitoring algorithm that enables operation of the other monitoring circuitry to ensure that the repetitious phenomena data sensed by the at least one sensor 201 is used to properly determine and monitor the particular phenomena.

The patient monitoring device 202 also includes front end circuitry 206 which selectively receives the input signal 203 from the at least one sensor 201 and generates electrical signals representative of the sensed phenomena data. A phenomenon detector 208 is electrically coupled to the front end circuitry 206 and selectively receives the electrical signals representative of the phenomena data therefrom. The phenomenon detector 208 implements at least one type of phenomena detection algorithm that uses the repetitious phenomena data of the input signal 203 to determine at least one particular type of patient phenomenon that used in patient monitoring. The phenomenon detector 208 is shown in FIG. 2 as a QRS detector for purposes of example only. However, one skilled in the art knows that detectors for detecting any phenomenon corresponding to any physiological patient parameter may be readily substituted.

A measurement processor 210 is electrically coupled to the phenomenon detector 208 and includes circuitry for determining a signal quality measurement associated with the input signal. For purposes of example only, the measurement processor 210 is shown as a stability processor and will be referred as such for the remaining description for FIGS. 2-6. The stability processor 210 automatically analyzes and determines a signal quality measurement based on the stability of the input signal sensed by the at least one sensor 201. The stability processor 210 dynamically determines a stability value of the input signal 203 by determining the stability of the sensed phenomena over a predetermined time period (e.g. a number of phenomena samples). The stability measurement is advantageously responsive to both non-physiological and physiological noise and determines if the input signal 203 is of sufficient quality to be used by the phenomenon detector 208 to determine and monitor at least one patient parameter. The stability processor 210 provides a feedback to the phenomenon detector 208 by using phenomena samples that have been determined by the phenomenon detector 208. The feedback enables the phenomenon detector 208 to automatically adjust the weighting assigned to the different input signals used thereby to determine the desired patient phenomena.

The stability processor 210 identifies a time period comprising a predetermined number of phenomena samples. For each phenomena sample, the stability processor 210 selects a particular feature of the phenomena sample and compares the similarity of the particular feature between respective phenomena samples, sample by sample, in the time period to determine a feature similarity value. In the event that the stability processor 210 determines that the feature similarity over the time period is above a first stability threshold, the signal quality of the input signal is high (ideal). A feature of a respective phenomena sample may include any points or points of that sample that can be compared to a same point on at least one of a preceding or subsequent phenomena sample allowing for a difference measurement to be determined between samples in the window. If the feature similarity over the time period is below the first stability threshold but above a second stability threshold, the signal quality is deemed acceptable and thus still able to be used by the phenomenon detector 208 but has a lower weight associated therewith. If the feature similarity is below the second stability threshold, the signal quality is deemed poor and the stability processor 210 signals the phenomena detector to disregard data in the particular input signal 203. The stability measurement is continually performed as each subsequent phenomena sample is determined by the phenomenon detector 208 thereby providing a continual measurement of signal quality over time. This advantageously increases the responsiveness of the phenomena detection and monitoring to automatically adjust the set of input signals from the set of sensors that are used in determining and monitoring the desired repetitious phenomena.

While input signals that have been deemed poor quality and thus not desirable for use in subsequent phenomena determination by the phenomenon detector 208 are disregarded, phenomena samples are continually determined for the particular input signal 203 to continually check if the signal quality has increased and is either ideal or acceptable and thus able to be re-incorporated as an input to the phenomena detection algorithm.

Once data representing the repetitious phenomena is determined by the phenomenon detector 208, the control processor 204 may use the high quality repetitious phenomena data for determining and monitoring at least one patient parameter. The control processor 204 may cause the determined and monitored patient parameter data derived from the repetitious phenomena data to be displayed on a display unit 212. Alternatively, the control processor 204 may analyze the repetitious phenomena data to determine if the repetitious phenomena data has reached or exceeded a particular alarm threshold indicative of a patient condition that needs immediate attention. If the threshold has been reached or exceeded, the control processor 204 may signal an alarm unit 214 to generate an alert that may be received by a healthcare professional notifying the healthcare professional that the patient is in need of care. The signal quality measurement used to selectively and dynamically control the source of input for determining a particular phenomena is particular advantageous in the case of determining if the sensed phenomena is indicative of a particular medical condition because a higher quality signal is directly proportional to the ability to accurately detect an alarm condition for a particular patient. In another embodiment, the control processor 204 may initiate a communication across a network 216 to provide the repetitious phenomena data to a remote computer system 218. The network 216 may be at least one of a wide area network or a local area network and enable connection of the patient monitoring device 202 via wired or wireless communication protocols. The remote system 218 may include at least one of (a) a central monitoring station; (b) a heathcare information system (HIS); (c) a computer at a remotely located physicians office; (d) a portable communication device (e.g. cell phone; smartphone; tablet, etc); (e) a patient record system; and (f) a cloud based repository of patient information accessible via the internet.

In an exemplary embodiment, the patient monitoring device 202 described in FIG. 2 is a ECG monitoring device and the at least one sensor 201 are electrodes selectively connected to a patient in known locations. In this embodiment, the repetitious phenomena is ECG data and the phenomenon detector 208 is a QRS detector for detecting QRS complexes in the ECG data sensed by the at least one sensor 201. The operation of the stability processor 210 in this embodiment will be described hereinbelow with respect to FIGS. 3-6.

Figure 3:
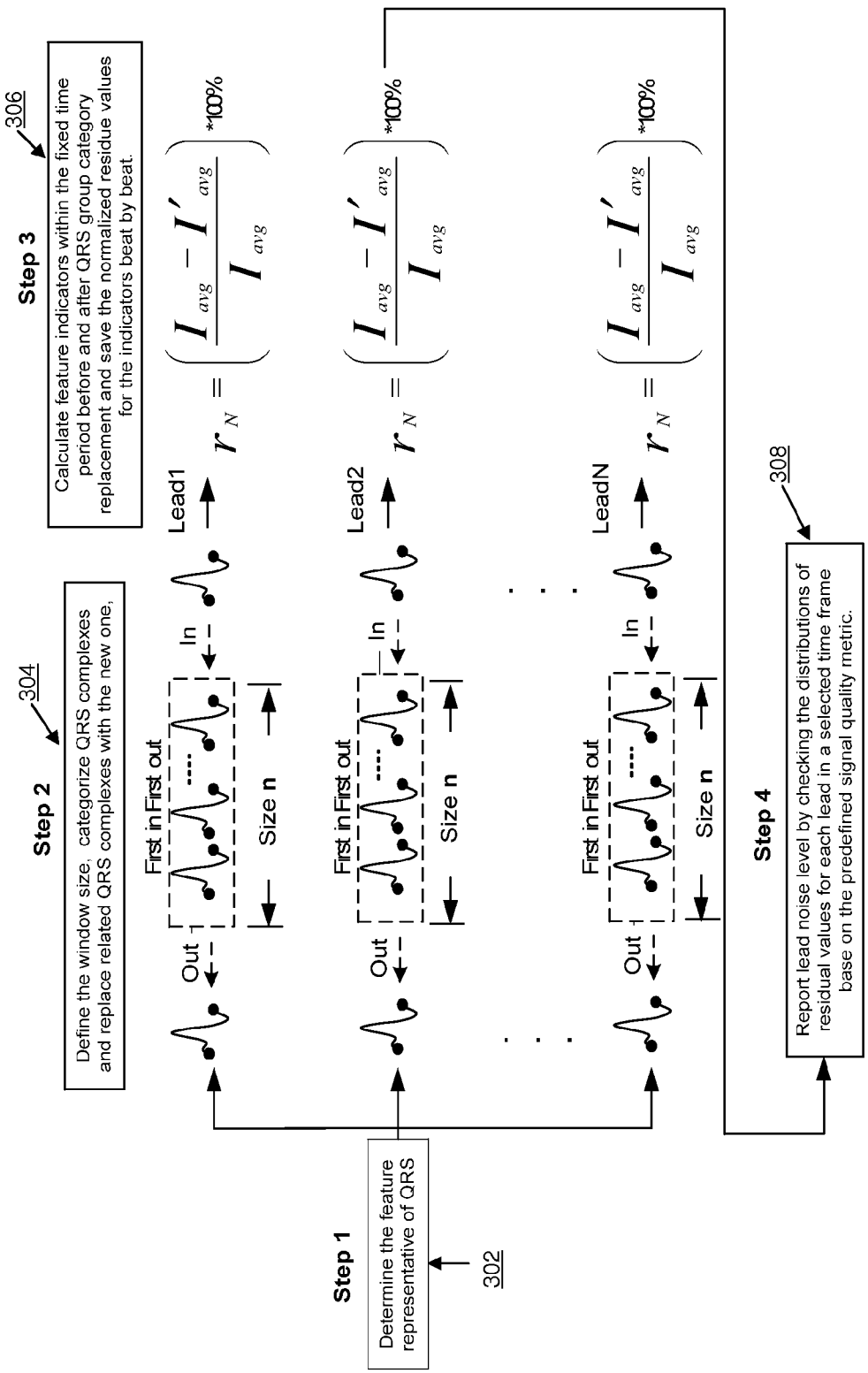
FIG. 3 is a flow diagram detailing the operation of a first embodiment of the signal quality measurement system according to invention principles.

The stability processor 210 in FIG. 2 advantageously measures the quality for a given single lead by analyzing the stability of QRS complexes dynamically over a time period window wherein the window includes a predetermined number of previously determined QRS complexes using only the given single lead. FIG. 3 depicts an exemplary flow diagram detailing the stability analysis algorithm. Unlike previous noise level determinations that were made using the morphology features measurement of each individual QRS complex, the algorithm described in FIG. 3 uses the feature similarity of a particular QRS feature for a group of QRS complexes. The key in this quantitative assessment of noise level is to check the feature similarity of QRS complexes over a fixed time period window complex by complex (e.g. beat by beat). If the feature similarity level is high over a time period, the ECG signal quality is high. On the other hand, low feature similarity indicates a noisy ECG signal.

Figure 4:
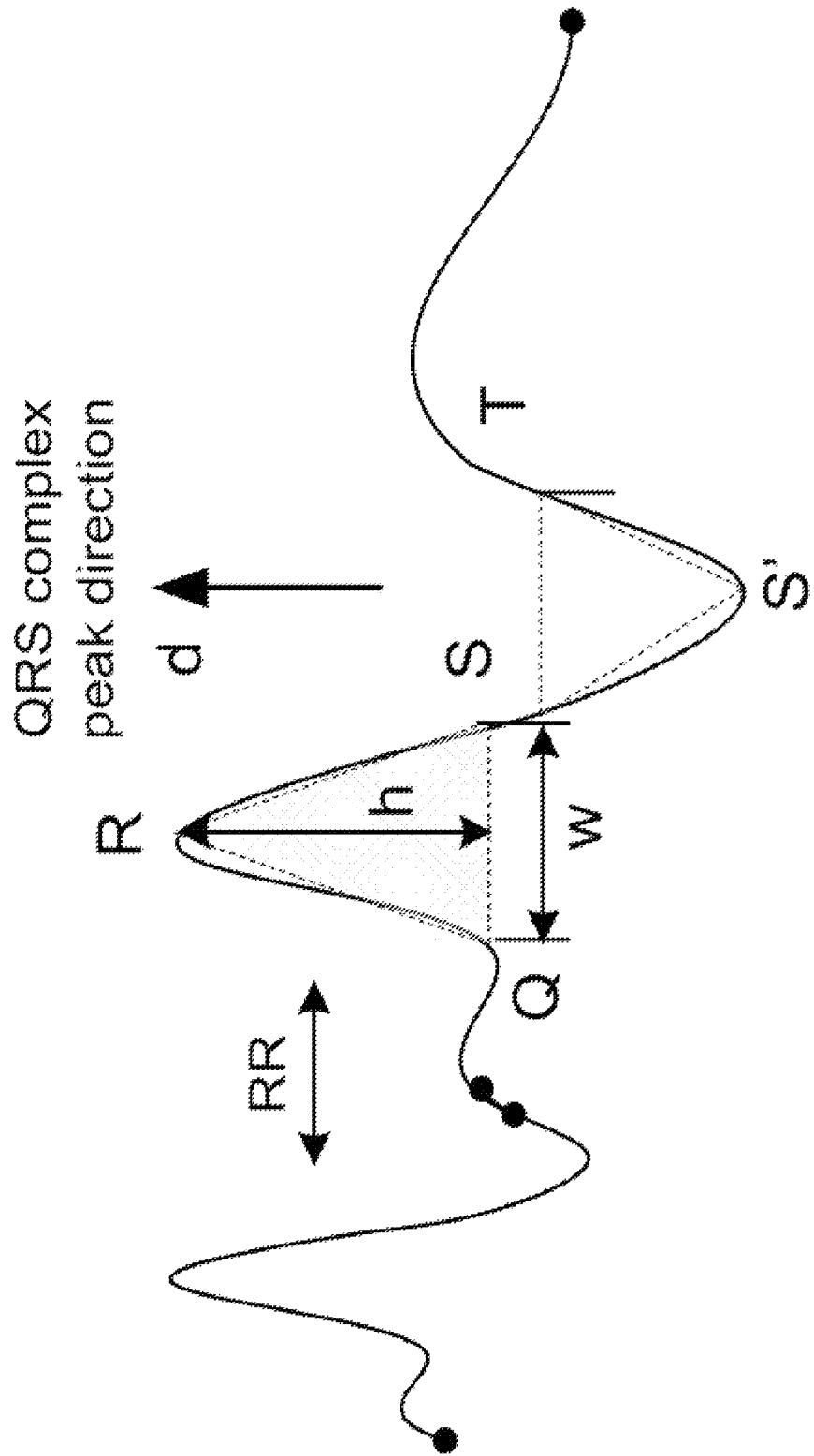
FIG. 4 is an exemplary ECG waveform showing different features of a QRS complex according to invention principles.

In step 302 the stability processor determines at least one feature representative of a QRS complex for use as a comparison point for identifying feature similarity between successive QRS complexes of a predetermined group of QRS complexes. Exemplary features used to delineate a QRS complex are shown in FIG. 4 and include any of:

(a) h: The height of QRS
(b) w: The width of QRS
(c) ΔQRS: The triangle area of QRS
(d) ΔSS'T: The triangle area of ST-Segment
(e) d: Peak direction of QRS
(f) RR: RR interval The features shown in FIG. 4 are for purposes of example only and measurement of any point within a particular QRS complex or between respective QRS complexes may be used as a feature for which the feature similarity may be checked by the stability processor 210. The selected feature is then used to check the feature similarity for that feature in respective input signals derived from respective sensors connected to the patient. As shown herein, a signal quality measurement is determined by stability analysis for three input signals. However, this is shown for purposes of example only to illustrate the operational principles of the stability analysis algorithm. In particular, common ECG monitoring configurations employ four or five patient connected sensors from which data are combined to generate QRS complexes for the patient.

The following description and results are based using two selected features including (a) the triangle area of ΔQRS as determined below in equation 1

$$\Delta QRS = \frac{1}{2} \cdot h \cdot w \tag{1}$$

where h is the height and w is the width of QRS complex; and (b) and the peak direction of the QRS complex. By checking the peak direction of the QRS complex, the system advantageously ensures that any difference in the QRS area comparison is valid. The peak direction comparison serves as a check to ensure that the difference in area between successive QRS complexes could validly be interpreted as noise. If the peak direction between two samples is different, then the difference between the area of those QRS complexes would be significant and may cause the system to inappropriately determine the presence of noise. Thus, a peak direction comparison between QRS complexes ensures that any difference between the at least two feature is not a false positive for noise on the signal.

Upon determining the feature in step 302, the stability processor 210 automatically determines a size N of continuous QRS complexes in the predetermined group of complexes defining a window. Thus, N represents the number of complexes of the window. Once the window size is determined, the stability processor 210 averages each determined feature representative of all detected QRS complexes in the window. Continuing with the determined feature described above being peak direction and ΔQRS, the stability processor 210 compares the peak direction of the QRS complexes in the window. If the peak direction is determined to be the same, the averaged feature representation of ΔQRS of all detected complexes in the window can be calculated using equation 2 below which states $$I_{avg} = \frac{1}{2} * \left( \frac{\sum_{i=1}^{N}(h_i * w_i)}{N} \right) \tag{2}$$

Figure 5:
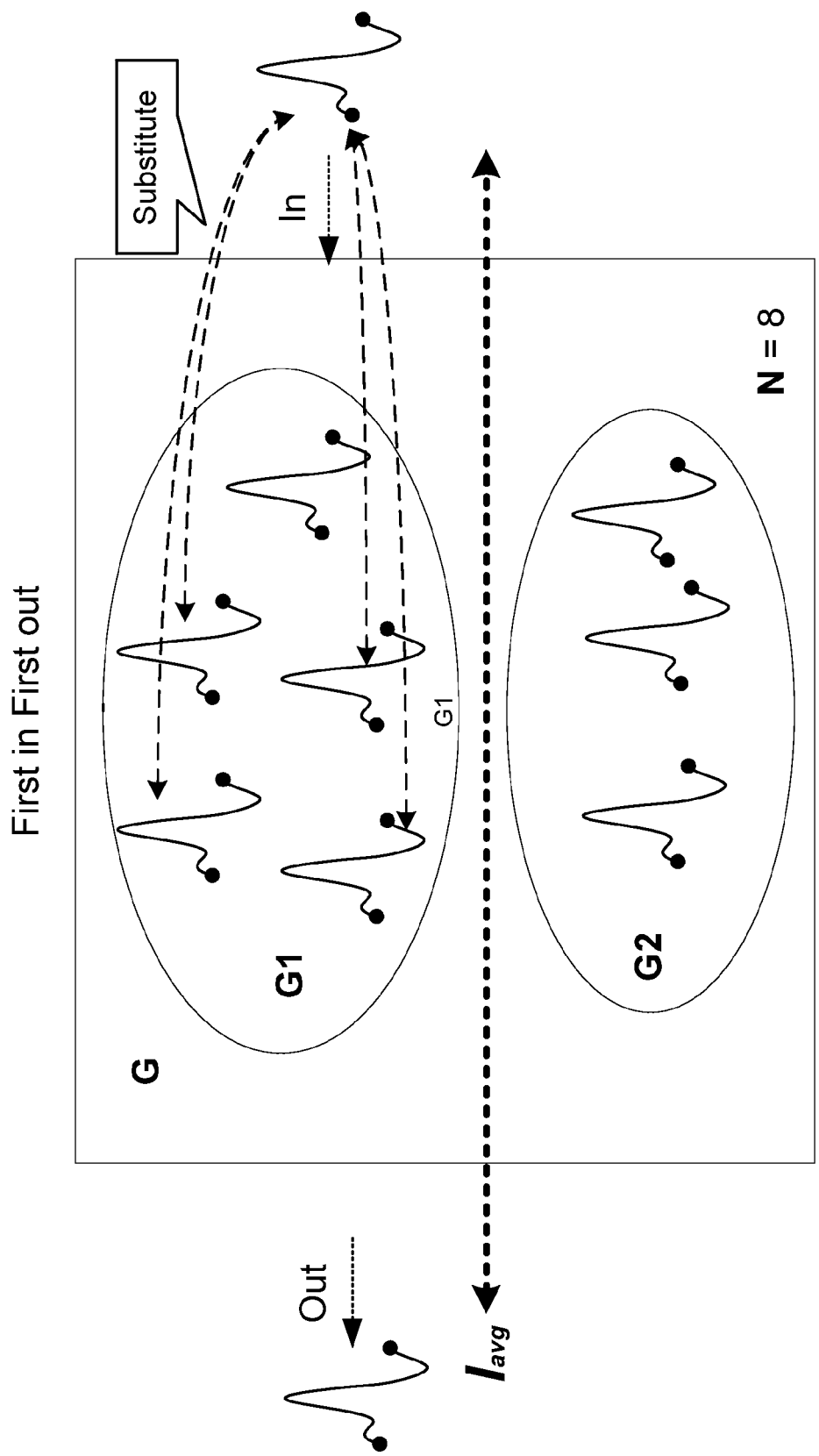
FIG. 5 depicts an aspect of the first embodiment of the signal quality measurement system showing the categorization and substitution of QRS complexes according to invention principles.

If the peak direction between complexes in the window is determined to be different, the stability processor advantageously determines the ΔQRS for the complexes having the same peak direction and substitutes QRS complexes in the window having different QRS peak directions with later occurring QRS complexes having the same QRS peak direction. Once the average feature is calculated, the system categorizes and replaces respective QRS complexes in a first in, first out manner. This categorization of QRS complexes is shown in FIG. 5. Referring now to FIG. 5, the group of QRS complexes is categorized into two subgroups G1 and G2 and replacement is performed as follows:

For any QRSi∈ G1, If ΔQRS≥Iavg.
For any QRSj∈ G2, If ΔQRS<Iavg.

where 0≤i, j≤N and N is the size of the group, i is the individual complexes within the window and j represents the number of different input signals from respective leads. Thus, an exemplary manner for determining if a replacement of a complex is required is described in equation 3 which shows $$\Delta QRS(i) = \begin{cases} \Delta QRS(In) & \text{If both the areas of } \Delta QRS(i) \text{ and } \Delta QRS(In) \leq Iavg \text{ with the same peak direction} \\ & \text{Or} \\ & \text{If both the areas of } \Delta QRS(i) \text{ and } \Delta QRS(In) \geq Iavg \text{ with the same peak direction} \\ \Delta QRS(i) & \text{Otherwise} \end{cases} \tag{3}$$

where QRS(in) is the latest detected QRS complex, QRS(i) is the existing QRS complex in the group. Thus, if the ΔQRS of the existing complex is equal to the ΔQRS of the incoming latest QRS complex, no replacement is needed. However, any deviation of ΔQRS between the existing and latest QRS complexes results in replacement of the oldest QRS complex in time with the latested QRS complex QRS(In).

Referring back to FIG. 3, the stability processor recalculates the averaged feature representative I'avg of the new subgroup of complexes in accordance with equation 4 which states $$I'_{avg} = \frac{1}{2} \cdot \left( \frac{N1 \cdot h(in) \cdot w(in) + \sum_{i=0}^{N2} h_i \cdot w_i}{N} \right) \tag{4}$$

where N1 is the number of QRS complexes in G1 that are replaced by QRS(in) and N2 is the size of G2, h(in) is the height of QRS(in), w(in) and is the width of QRS(in), hi is the height for QRS(i) and wi is the width for QRS(i) and where 0≤i≤N2 and N1+N2=N.

Once the value of I'avg has been calculated, the stability processor 210 automatically normalizes the averaged feature representative Iavg for each QRS complex (or beat) in accordance with equation 5 to derive an $r_N$ value that corresponds to a stability value for the particular input signal coming from the respective sensor (e.g. ECG lead). The value of $r_N$ is the absolute value thereby accommodating positive and negative feature variations and ensuring proper normalization thereof. The determination of $r_N$ is shown in Equation 5 which states $$r_N = \left(\frac{I_{avg} - I'_{avg}}{I_{avg}}\right) \times 100\% \quad (5)$$

Figure 6:
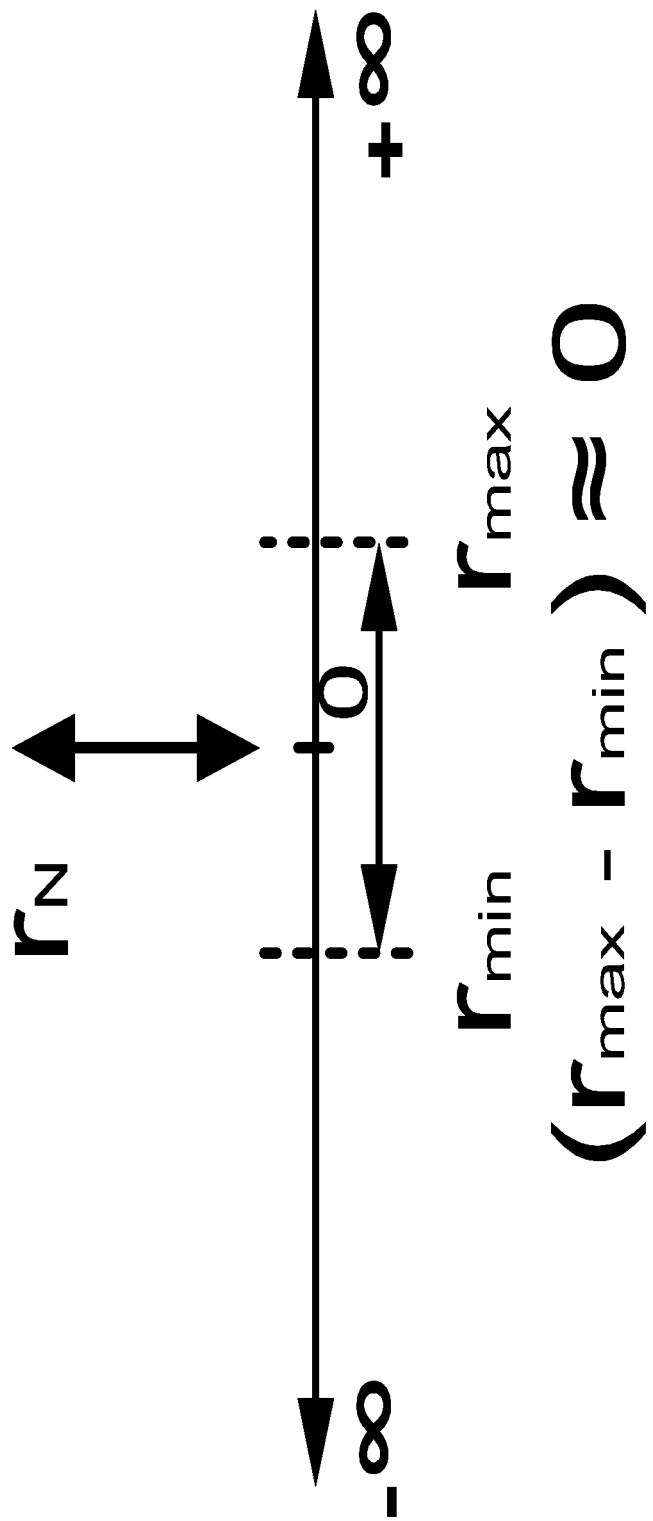
FIG. 6 shows a graphical depiction of a distribution range of $r_N$ that is associated with a clean signal according to invention principles.

The $r_N$ value representing signal quality (e.g. noise) for each input signal is calculated and, in step 308, the signal quality is checked by comparing the $r_N$ value with a distribution of residual $r_N$ values for each lead in the selected time frame using this signal quality metric calculated in accordance with Equation 5. This process is shown in FIG. 6. FIG. 6 is a plot showing the distribution range of potential $r_N$ values that would be deemed acceptable based on the determined feature variability of the feature within the defined window. The acceptable range includes $r_N$ values that fall between the range defined as rmin and rmax which straddle zero. Thus, as shown in FIG. 6, if the signal is clean, the QRS complex feature is stable for the group (at least for a short period time window) and thus falls within the distribution range defined by rmin and rmax, where rmin is substantially equal to −30 and rmax is substantially equal to 30. An input signal falling within this distribution range is determined by the stability processor 210 to be acceptable for use by the QRS detector in calculating subsequent QRS complexes to be used in patient monitoring.

Upon determining that the input signal is of sufficient quality by checking that the $r_N$ value falls within the distribution range defined by $r_{min}$ and $r_{max}$, the stability processor 210 assigns the respective input signal with a stability coefficient corresponding to a weight proportional to the stability of the signal which is used by a multi-lead QRS detection algorithm in determining the QRS complexes that are monitored by the ECG monitoring device. An input signal having an $r_N$ value between a first threshold and zero is determined to be of high quality and thus a maximum stability coefficient is associated with the respective input signal. An input signal having an $r_N$ value between the first threshold and at least one of $r_{min}$ and $r_{max}$, is determined to still be acceptable but has a medium stability coefficient with a value less than the maximum stability coefficient associated therewith. This results in data from an input signal having a medium coefficient associated therewith being used less by the multi-lead QRS detection algorithm. An input signal having an $r_N$ less than $r_{min}$ or greater than $r_{max}$, is determined to be of low quality and a minimum stability coefficient is associated therewith. Assigning an input signal with a minimum stability coefficient results in the multilead QRS detection algorithm disregarding data derived from that particular sensor and calculates the resulting QRS complexes using data from leads having either the high stability coefficient or a medium stability coefficient. The weighting associated with the high, medium and low stability coefficients is represented by a weight contributor $W_{rn}$ of rn for each lead as defined in equation 6 as the follows:

$$W_{rn} = \begin{cases} 1 & \text{If } 0 \leq r_N \leq 15 \\ 0.75 & \text{If } 15 < r_N \leq 30 \\ 0 & \text{If } r_N > 30 \end{cases} \quad (6)$$

The maximum stability coefficient of 1 is assigned when the stability of the signal defined by the feature variability of the determined feature (rn) is between 0 and 15% of a baseline value (Iavg). The medium stability coefficient of 0.75 is assigned when the stability of the signal defined by the feature variability of the determined feature (rn) is between 15% and 30% of the baseline value (Iavg). The minimum stability coefficient of 0 is assigned when the stability of the signal defined by the feature variability of the determined feature (rn) is greater than 30% of the baseline value (Iavg).

Once the stability coefficients for each input signal are determined the QRS detector generates a combined input signal including data derived from sensors that include either a high stability coefficient or a medium stability coefficient. Thus, the QRS detector operates in accordance with Equation 7 to develop the combined signal. Equation 7 provides $$comb[i] = \frac{\sum_{j=1}^{N} QRS\_Amplitude\_Average[i,j] \times s[i,j] \times W_m[j]}{\sum_{j=1}^{N} QRS\_Amplitude\_Average[i,j]} \quad (7)$$

The weight contributor $W_{rn}[j]$ of rn (j=1, 2 ... n) is updated beat by beat. Where n is the maximum number of leads for the current processed ECG signal. This ensures that the subsequently determined QRS complexes by the QRS detector have been determined using input signal of the highest quality resulting in higher quality patient monitoring data.

The stability measurement described above with respect to FIGS. 3-6 includes the following constraints thereby showing the effectiveness of the stability analysis in determining a signal measurement associated with a respective input signal for use and application in multi-lead QRS detection. The exemplary signals used are from the two-channel MIT-BIH and NST (The Noise Stress Test Database) databases. The tests are done against different clinical situations (e.g. normal, noise and arrhythmia) and included the following preselected constraints:
  (a) N=8, N is the size of continuous QRS complexes group.
  (b) For any QRSi∈ G1 and QRSj∈ G2, let Ti and Tj denote the time stamps of QRSi and QRSj respectively. The QRSi and QRSj are selected as valid QRS complexes for calculation if |Ti−Tj|≤8 (seconds). Where 0≤i, j≤N.
  (c) Two features of the QRS complex were selected for comparison: The triangle area of ΔQRS (equation 1) and the peak direction of the QRS complex.
  (d) Let rn=100 (or −100) if rn≥100 (or ≤−100). In each distribution plot of rn, the vertical axis represents the percentage of rn (range from −100 to 100%), and the horizontal axis is the scaled time frame.

Figure 7:
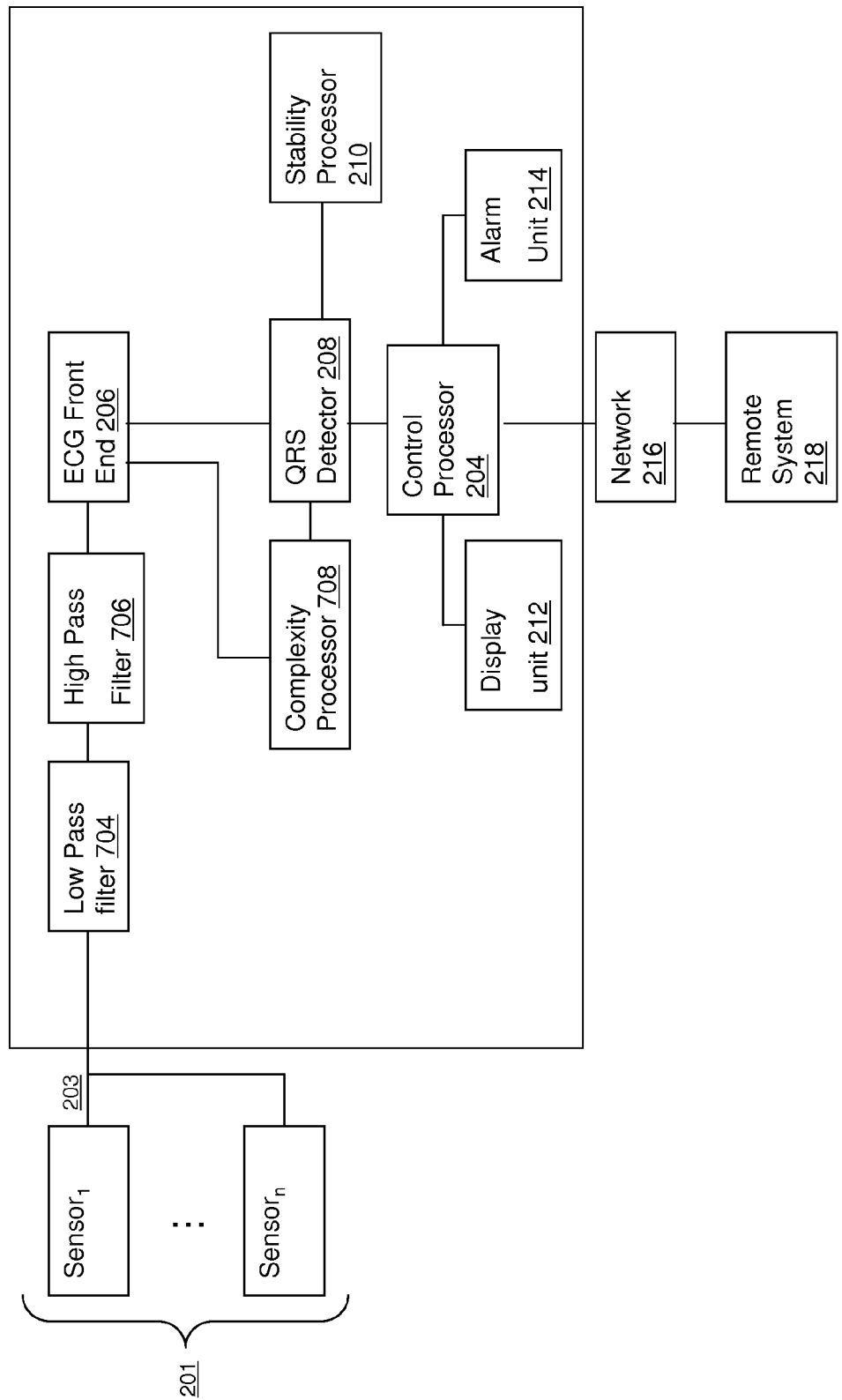
FIG. 7 is a block diagram of an ECG monitor including a second embodiment of a signal quality measurement system according to invention principles.
Figure 8:
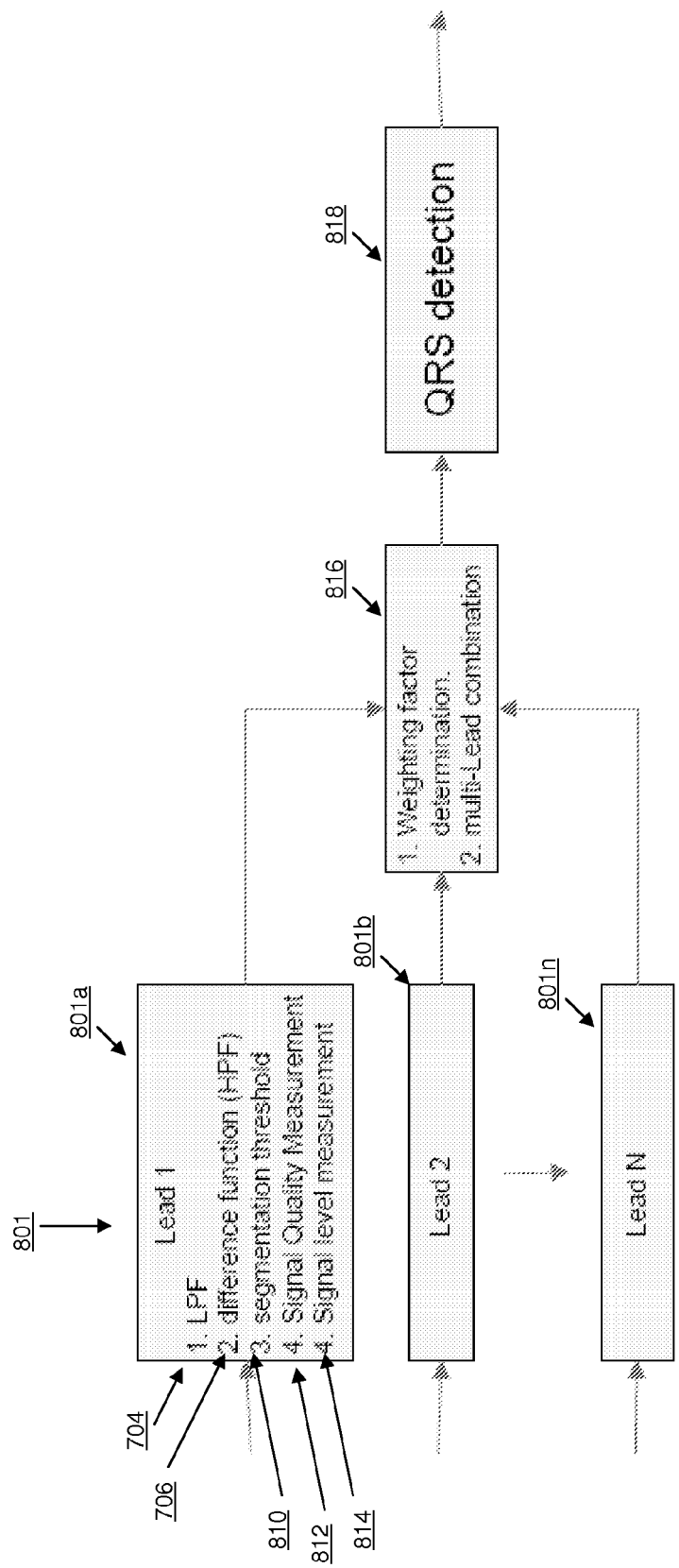
FIG. 8 is a block diagram detailing the workflow for measuring the signal quality in a multi-lead QRS detection system according to invention principles.

Another embodiment of the signal quality measurement system is shown in FIGS. 7 and 8. This embodiment employs a second signal quality measurement used to identify a noisy input signal. The second signal quality measurement is determined in real-time prior to being processed by the patient monitoring device. The second signal quality measurement is associated with a complexity of the respective input signal. When visually inspecting an input signal, one of the first impressions to the observer is that of their "complexity" whereby input signals that are random are deemed complex and may be indicative of noise while other input signals may demonstrate a reappearance of certain patterns. Thus, signal complexity is an intuitive description and may be quantified for purposes of interpreting the input signal quality by quantifying signal complexity using a signal complexity metric.

An exemplary patient monitoring device that employs the second signal quality measurement is shown in FIG. 7. FIG. 7 is a patient monitoring device similar to one described above in FIG. 2 and thus includes similar features and components described above. The like components are similarly numbered and thus include at least the functions described above in FIG. 2. Thus, similarly to the monitoring device 202 in FIG. 2, this embodiment of the patient monitoring device 702 includes at least one sensor 201 connected thereto. The at least one sensor 201 may be connected to a particular location on the body of a patient for use in sensing data corresponding to a repetitious phenomena exhibited by the patient. The at least one sensor 201 senses a particular type of repetitious phenomena from the patient which is used as an input signal 203 by the patient monitoring device 702. The patient monitoring device 202 includes a control processor 204 that selectively controls the operation thereof. The control processor 204 executes at least one type of monitoring algorithm that enables operation of the other monitoring circuitry to ensure that the repetitious phenomena data sensed by the at least one sensor 201 is used to properly determine and monitor the particular phenomena.

In addition to the hardware components shown in FIG. 2, the patient monitoring device 702 able to perform the second signal quality measurement also includes a low pass filter 704 and a high pass filter 706 coupled to respective sensors 201 for filtering the input signals prior to measuring the signal quality as well as prior to being processed by the phenomenon detector 208. For each input signal 203 sensed by a respective sensor 201, the low pass filter 704 filters the input signal 203 in a known manner. The filtered signal is further filtered by the high pass filter 706. Filtering by the high pass filter 706 may include a summation of absolute first and second differencing operations performed on respective phenomena samples contained in the input signal 203 to generate a positive differencing signal, the signal quality of which may then be determined. In one embodiment, the repetitious phenomena sensed by the at least one sensor is ECG data and the filtering operation performed by the high pass filter may include filtering ECG signal samples (a sampling rate of 250 Hz) to generate the positive differencing signal.

The filtered input signal 203 is then transformed by the front end circuitry 206 in a known manner to produce an electrical signal representative of the repetitious phenomena. The second signal quality measurement may also be performed by a measurement processor 708 which may include circuitry for determining a signal quality measurement associated with the input signal. For purposes of example, the measurement processor 708 will be referred to as a complexity processor 708 which is able to determining the signal quality using a second signal quality measurement metric. The remaining description of FIGS. 7 and 8 will refer to the measurement processor 708 as complexity processor 708. The complexity processor 708 is electrically coupled to the front end circuitry 206 and the phenomenon detector 208. The complexity processor 708 automatically evaluates the filtered input signal 203 by evaluating the randomness of finite sequences using a complexity metric. In one embodiment, the complexity metric used is the Lempel and Ziv (LZ) complexity metric which is an algorithm that has been used in information theory. The complexity processor 708 determines, in real-time, LZ complexity analysis for use as a scalar complexity metric in interpreting the ECG signal quality. The workflow detailing the operation of the complexity determination algorithm will be discussed below with respect to FIG. 8 whereby the patient monitoring device 702 is an ECG monitor.

In this embodiment, monitoring an ECG of a particular patient is performed by connecting a plurality of sensors 201 (e.g. electrodes) to known locations on the body of the patient to derive ECG lead data therefrom. In one example, the regular ECG leads are 3-lead, 5-lead, 6-lead, derived 12-lead, 12-lead. However, the signal quality need only be measured on Lead I, II, and V1-V6 because the data derived from these leads are used to calculate data associated with Lead III, aVR, aVL, and aVF using the standard Einthoven and Goldberger equations as is known in the art.

Referring now to FIG. 8, a plurality of patient connected sensors $801a$, $801b$ ... $801n$ are shown, collectively referred to using reference numeral 801. The sensors 801 represent electrodes coupled to a patient for use in sensing data representative of a patients heartbeat (e.g. a repetitious phenomena). ECG data is pre-processed by the low pass filter 704 and the high pass filter 706 as discussed above in FIG. 7. Additionally, a segmentation threshold analysis 810 is performed. The segmentation threshold analysis results in the transformation of the ECG signal into a binary sequence. As described below, a segmentation threshold level is provided and ECG data determined to be below the segmentation threshold is assigned the value of "0" and ECG data determined to be above the segmentation threshold is assigned the value of "1". A signal level (e.g. strength) analysis 812 is also performed whereby the amplitude of the ECG signal is compared to a threshold to ensure that the signal being analyzed is of sufficient strength. Thereafter, a signal quality measurement 814 is performed on the ECG data sensed by the sensors 801. The complexity processor 708 performs the signal quality measurement 814 using a complexity metric to assess the randomness of the signal to determine if noise is present therein. The following is a description of the operation of the complexity processor 708 in determining if noise is present on the input signal.

The complexity measurement is represented by the variable c(n) where c represents the complexity and n length of the ECG data in a particular input signal. Prior to employing the LZ complexity measurement algorithm to determine c(n), the ECG signal must be transformed into a finite symbol sequence. Typically the ECG signal is converted into a binary sequence because previous studies have shown that 0-1 conversion is adequate to estimate LZ complexity in biomedical signals.

Consider a 0-1 string $P=s_1, s_2, s_3, \ldots s_n$, where $s_i$ is the character 0 or 1, I=1, 2, ... n, where n is the length of ECG data. The complexity processor 708 determines and selects a length of ECG data to be analyzed and defines this length as the window length (WL). In one embodiment, WL is set equal to four (4) seconds which typically includes substantially 500 samples. The sampling rate may be reduced to save computation power. For example, the sampling rate may be reduced by at least half resulting in the WL having a sampling rate of 250 samples. The complexity processor 708 automatically compares the ECG signal data with a threshold and converts the ECG data signal into a binary sequence (0-1) using a mean of substantially 500 data samples in a known manner. Using a mean of substantially 500 data samples is particularly advantageous as the threshold because of its robustness to outliers.

Due to the nature of ECG data, there are some threshold issues observed in ECG data that may have a significant negative impact on signal complexity measurement. Thus, the complexity processor 708 must correct for these threshold issues prior to calculating the complexity measurement of the signal. In particular, there are small root noises in differencing signal that reduce the mean value of the data points within the window and, if not accounted for, would artificially increase signal complexity. To account for the small root noises in the ECG data, a sticky-zero threshold is adjusted to the maximum data point within the time window and applied first to remove these small noises in differencing signal.

The complexity processor 708 then determines a final threshold value for use in the complexity measurement. In order to find the desired threshold value, the final mean value of the data points between a first mean value and a second mean value of the data points are used to transform ECG signal into 0-1 string. In one embodiment, the first mean value is substantially 85% mean value and the second mean value is substantially 115% mean value which was determined by an empirical study of ECG data. The complexity processor 708 selects a data point corresponding to a sample in the window that has the lower mean value but which is also present in the binary string as a "1". This manner of selecting the final threshold value for use in determining the complexity of the input signal advantageously accounts for ECG data with a big T wave or multiple P waves (atrial fibrillation/flutter) that may have mean threshold values that are low would erroneously result in identifying the signal as complex (e.g. noisy) even when the ECG signal is relatively clean.

The complexity processor 708 then calculates the complexity of the input signal using the LZ complexity algorithm. The transformed binary sequence P=$s_1, s_2, s_3, \ldots s_n$ (where, $s_1, s_2$, etc. denote characters, 0,1, and n=signal length) is scanned from left to right. The complexity processor 708 includes a complexity counter c(n) which is increased by one unit every time a new subsequence of consecutive characters is encountered in the scanning process. The complexity measure can be estimated using the following algorithm:

1) Let S and Q denote, respectively, subsequence of the sequence P=$s_1, s_2, s_3, \ldots s_n$, and SQΠ be the concatenation of S and Q. Sequence SQ is derived from SQ after its last character is deleted (Π means the operation to delete the last character in the sequence). Let V(SQΠ) denote the vocabulary of all different subsequences of SQΠ such that at beginning of the sequence, c(n)=1, S=$s_1$, Q=$s_2$. Thus, SQΠ=$s_1$.
2) For generalization, now suppose S=$s_1, s_2, \ldots s_r$, Q=$s_{r+1}$ then SQ=$s_1, s_2, \ldots s_r$. If Q∈ V(SQΠ), then Q is the subsequence of SQΠ, not a new sequence.
3) S need not change and now renew Q to be $s_{r+1} s_{r+2}$, then judge if Q belongs to V(SQΠ) or not.
4) Repeat the previous steps until QV not ∈ (SQΠ). Now Q=$s_{r+1}, s_{r+2}, \ldots, s_{r+i}$ is not a subsequence of SQΠ=$s_1, s_2, \ldots s_r, s_{r+1}, \ldots s_{r+i-1}$ so increase c(n) by one.
5) Thereafter, combine S with Q and S is renewed to be S=$s_1, s_2, \ldots s_r, s_{r+1}, \ldots s_{r+i}$, at the same time take Q as Q=$s_{r+i+1}$.

The above algorithm is repeated until Q is the last character. At this time, the number of difference subsequences present in binary sequence P is c(n) thereby providing a complexity measurement value. The c(n) measures the number of the distinct patterns contained in the sequence with only two simple operations (comparison and accumulation).

However, in addition to determining the complexity of a finite sequence, the complexity processor 708 is advantageously able to determine a complexity measure which is independent of the sequence length by normalizing c(n). The normalization is described below. For example, if the length of the sequence is n and the number of different symbols in the symbol set is a, it has been approved that the upper bound of c(n) is given by the equation shown in Equation 8 which states $$c(n) < b(n) = \frac{n}{(1 - \varepsilon_n)\log_\alpha(n)} \quad (8)$$

where $$\varepsilon_n = 2\frac{1 + \log_\alpha(\log(\alpha n))}{\log_\alpha(n)}$$

For a 0-1 sequence (e.g. binary), α=2. Thus, the complexity can be normalized in accordance with Equation 9 which states:

$$C(n) = \frac{c(n)}{b(n)} \quad (9)$$

Upon determining the complexity measurement value for respective input signals derived from respective sensors, the complexity measurement value is compared to the final mean threshold value determined above and, if the complexity measurement exceeds the final mean threshold value, then the input signal is determined to be complex and is indicated as noisy. The complexity processor 708 also calculates a complexity coefficient representing a weighting factor applied to the respective input signal as shown in box 816. The weighting factor w(i) is 0≤w(i)≤1, i=1, 2 ... n and the Σw(i)=1. This results in the complexity coefficient being proportional to its measured quality based on complexity. The weighting factors are updated every 300 ms to allow for quick adaptation to signal quality changes. Since the QRS detection signal can dynamically adapt to the quality of the incoming ECG signal, the impact of noisy signals to QRS detection is minimized.

Furthermore, as the ECG monitor employs a multi-lead QRS detection algorithm represented in box 816, the complexity measurement value for each incoming input signal derived from respective sensors must be taken into account. To accomplish this, the complexity processor 708 provides the complexity measurement value for each input signal to the QRS detector as in box 818, the amplitude (signal level) of the QRS complex is calculated for each detected QRS complex on each lead and a separate running average (QRS amplitude_Average) for the QRS amplitude is kept for each ECG lead. The different leads are combined into a single signal for QRS detection in accordance with Equation 10 which states $$comb[i] = \frac{\sum_{j=1}^{N} QRS\_Amplitude\_Average[i, j] \times w[i, j] \times s[i, j]}{\sum_{j=1}^{N} QRS\_Amplitude\_Average[i, j]} \quad (10)$$

In Equation 10, comb[i] is the i-th sample of the combined ECG signal supplied at the output of proportional adder. QRS_Amplitude_Average[j] is the running average of the QRS amplitude on the j-th ECG lead, QRS_Amplitude_Average[i] is the i-th sample of the absolute value of total difference signal on the j-th ECG lead supplied at the output of a proportional adder and N is the total number of ECG leads. Additionally, w(i) is the weight associated with the i-th sample on the j-lead and s(i) is the complexity value on the i-th sample on the j-th lead.

The result of the process implemented by the equation is a summing of the QRS complexes, for those of the N leads that are used, in accordance with their relative weight based on signal quality (e.g. complexity value). The value of comb(i)

may be normalized by dividing the numerator by the sum of the running average of the QRS amplitudes on all of those of the N leads that are used. Combination of multiple ECG signals from different leads advantageously enhances this signal used in determining the QRS complexes thereby improving the quality of the signal for use by the QRS detector.

Referring back to FIG. 7, another embodiment of the measurement processor may advantageously include both the complexity processor 708 along with the stability processor 208. The respective operations of the complexity processor 708 and the stability processor 208 remain as discussed above. However, this embodiment advantageously enables multiple signal quality measurements to be made based on the stability of the input signal that has already undergone processing by the phenomenon detector 208 as well the complexity of the input signal prior to processing by the phenomenon detector 208. This advantageously provides two modes of signal quality measure which can be combined by the phenomenon detector 208 when selecting the sources of the input signal being used to determine the phenomena. Continuing with the above described examples wherein the phenomenon detector 208 is a QRS detector, the stability measurement value and the complexity measurement value associated with respective leads may be combined to select the source for calculating the QRS complexes being monitored in accordance with Equation 11.

$$comb[i] = \frac{\sum_{j=1}^{N} QRS\_Amplitude\_Average[i, j] \times w[i, j] \times s[i, j] \times W_m[j]}{\sum_{j=1}^{N} QRS\_Amplitude\_Average[i, j]} \quad (11)$$

In Equation 11, comb[i] is the i-th sample of the combined ECG signal supplied at the output of a proportional adder. QRS_Amplitude_Average[j] is the running average of the QRS amplitude on the j-th ECG lead, QRS_Amplitude_Average[i] is the i-th sample of the absolute value of total difference signal on the j-th ECG lead supplied at the output of the proportional adder and N is the total number of ECG leads. Additionally, w(i) is the weight associated with the i-th sample on the j-lead and s(i) is the complexity value on the i-th sample on the j-th lead and Wrn(i) is the stability measurement of the i-th samples on the j-th lead.

The result of the process implemented by the equation is a summing of the QRS complexes, for those of the N leads that are used, in accordance with their relative weight based on signal quality (e.g. complexity value). The value of comb(i) may be normalized by dividing the numerator by the sum of the running average of the QRS amplitudes on all of those of the N leads that are used. Combining multiple ECG signals from different leads advantageously enhance this signal used in determining the QRS complexes thereby improving the quality of the signal for use by the QRS detector.

Figure 9A:
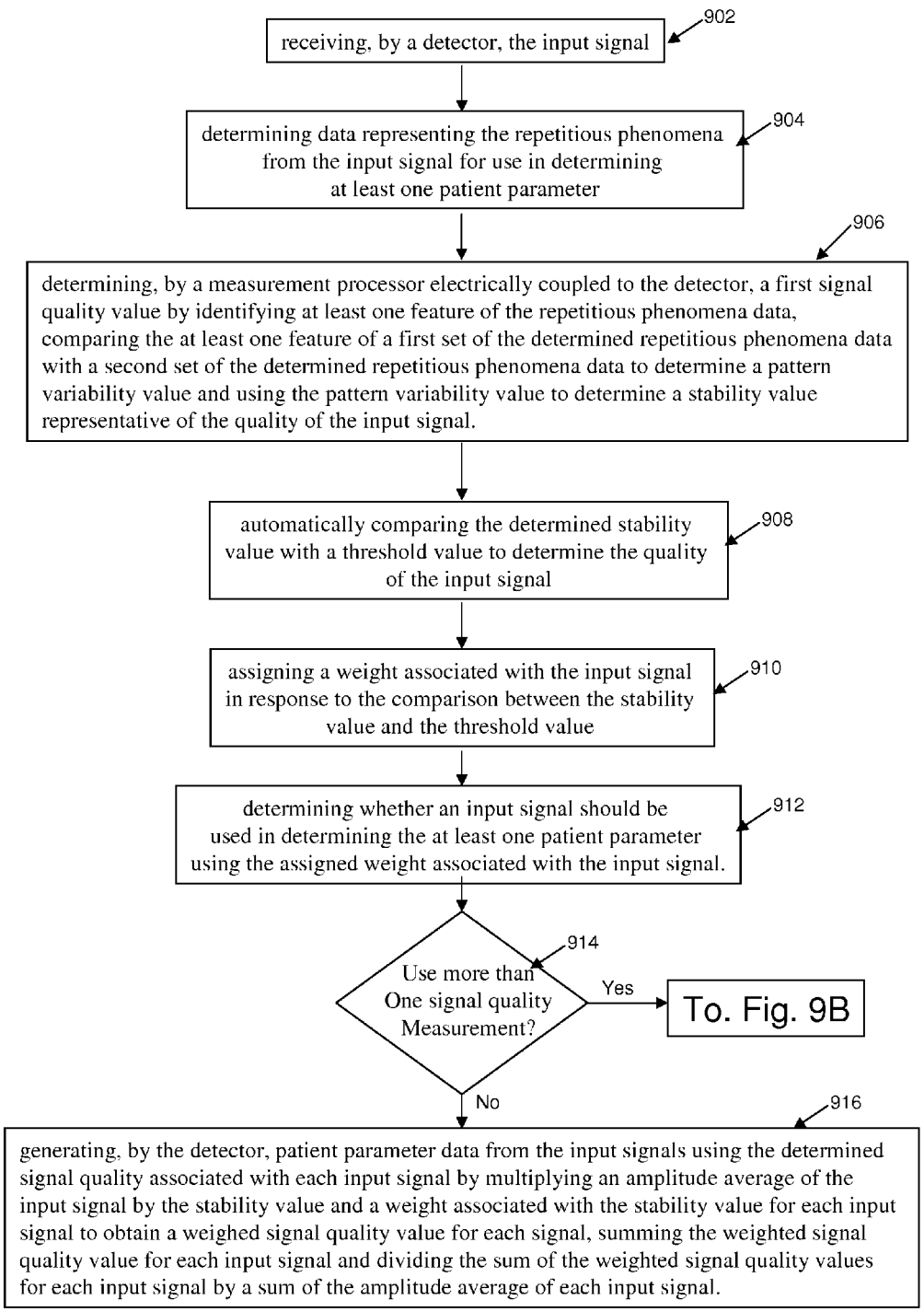
FIG. 9 is a flow diagram detailing the operation of the signal quality measurement system according to invention principles.
Figure 9B:
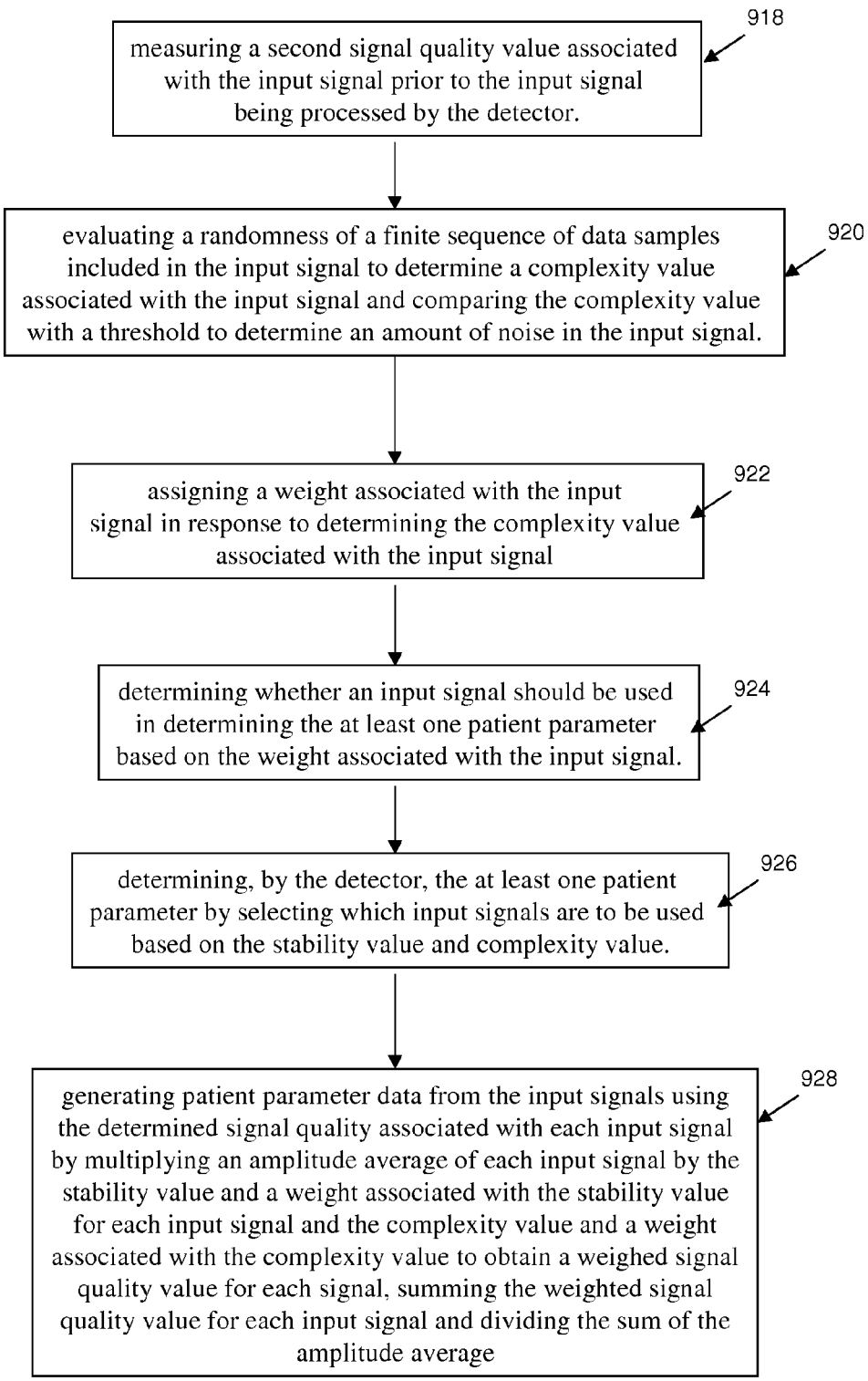

Exemplary operation of the system described above with respect to FIGS. 1-8 is shown in the flow diagram of FIGS. 9A & 9B. FIGS. 9A & 9B details a method of determining a signal quality of an input signal representing a repetitious phenomena derived from at least one sensor connected to a patient. In step 902, the input signal is received by a detector and, in step 904, the detector determines data representing the repetitious phenomena from the input signal for use in determining at least one patient parameter. In one embodiment, the repetitious phenomena data is ECG data and the activity of detecting detects QRS complexes from the ECG data.

In step 906 a measurement processor, which is electrically coupled to the detector, determines a first signal quality value by identifying at least one feature of the repetitious phenomena data, comparing the at least one feature of a first set of the determined repetitious phenomena data with a second set of the determined repetitious phenomena data to determine a feature variability value and using the feature variability value to determine a stability value representative of the quality of the input signal. In one embodiment, the at least one feature of the repetitious phenomena data includes at least one of (a) a height of a QRS complex; (b) a width of a QRS complex; (c) a triangle area of a QRS complex; (d) a triangle area of an ST-segment; (e) a peak direction of a QRS complex; and (f) an RR interval between successive QRS complexes.

In step 908, the determined stability value is automatically compared with a threshold value to determine the quality of the input signal. A weight associated with the input signal is assigned in response to the comparison between the stability value and the threshold value in step 910 and it is determined whether an input signal should be used in determining the at least one patient parameter using the assigned weight associated with the input signal in step 912. In one embodiment, the detector simultaneously detects repetitious phenomena data on a plurality of input signals being received from a respective sensor and measures the quality of the plurality of input signals. In step 914, the system queries whether or not the first signal quality value determined is the only signal quality value to use in selecting input signals. If the result of the query in step 914 is positive then the method continues in step 916. In step 916, the detector generates patient parameter data from the input signals using the determined signal quality associated with each input signal by multiplying an amplitude average of the input signal by the stability value and a weight associated with the stability value for each input signal to obtain a weighed signal quality value for each signal, summing the weighted signal quality value for each input signal and dividing the sum of the weighted signal quality values for each input signal by a sum of the amplitude average of each input signal.

Referring back to step 914, if the determination is negative indicating that a second signal quality measurement is to be used, the method continues in FIG. 9B at step 918. In one embodiment, the measurement of a second signal quality value associated with the input signal is performed prior to the input signal being processed by the detector. In step 920, a randomness of a finite sequence of data samples included in the input signal is evaluated to determine a complexity value associated with the input signal and the complexity value is compared with a threshold to determine an amount of noise in the input signal in step 922. In one embodiment, the evaluation process of step 922 includes converting the input signal into a binary signal, sequentially scanning the binary signal, incrementing a complexity counter by one upon detecting a change in a subsequence of consecutive characters in the binary signal, and comparing a value of complexity counter with a threshold to determine the complexity value associated with the input signal.

In step 924, a weight associated with the input signal is assigned in response to determining the complexity value associated with the input signal and the detector determines whether an input signal should be used in determining the at least one patient parameter based on the weight associated with the input signal in step 926 resulting in the detector determining the at least one patient parameter by selecting which input signals are to be used based on the stability value and complexity value.

In step 928, patient parameter data is generated from the input signals using the determined signal quality associated with each input signal by multiplying an amplitude average of each input signal by the stability value and a weight associated with the stability value for each input signal and the complexity value and a weight associated with the complexity value to obtain a weighed signal quality value for each signal, summing the weighted signal quality value for each input signal and dividing the sum of the weighted signal quality values for each input signal by a sum of the amplitude average of each input signal.

The apparatus described above with respect to FIGS. 1-9 advantageously determines at least one type of signal quality measurement that is used for determining at least one patient parameter being monitored by a patient monitoring device. The apparatus advantageously uses two different signal quality measurements taken at different times in order to select input signals having the highest quality thereby ensuring that the resulting patient parameter being monitored is also of the highest quality. This also improves the ability of the patient parameter being used for purposes of diagnosis because, in view of the high quality of the input signal from which the patient parameter is derived, the likelihood of false positives is reduced. Thus, the signal quality measurement system dynamically determines the signal quality of respective input signals in real-time and automatically updates the weight in which respective input signals are given in parameter calculation using multiple input signals such as a multilead QRS detection algorithm.

Although the invention has been described in terms of exemplary embodiments, it is not limited thereto. Rather, the appended claims should be construed broadly to include other variants and embodiments of the invention which may be made by those skilled in the art without departing from the scope and range of equivalents of the invention. This disclosure is intended to cover any adaptations or variations of the embodiments discussed herein.

What is claimed is:

1. An apparatus for determining a signal quality of an input signal representing a repetitious phenomena derived from at least one sensor connected to a patient comprising: a detector that receives the input signal and determines data representing the repetitious phenomena from the input signal for use in determining at least one patient parameter; a measurement processor electrically coupled to the detector that determines a first signal quality value by identifying at least one feature of the repetitious phenomena data and compares the at least one feature of a first set of the determined repetitious phenomena data with the at least one feature of a second set of the determined repetitious phenomena data to determine a feature variability value and using the feature variability value to determine a stability value representative of the quality of the input signal, wherein said measurement processor measures a second signal quality value associated with the input signal, the second signal quality value being measured prior to the input signal being processed by the detector, the second signal quality value is determined by evaluating a randomness of a finite sequence of data samples included in the input signal to determine a complexity value associated with the input signal and comparing the complexity value with a threshold to determine an amount of noise in the input signal, and said measurement processor evaluates the randomness of the input signal by converting the input signal into a binary signal, sequentially scanning the binary signal, incrementing a complexity counter by one upon detecting a change in a subsequence of consecutive characters in the binary signal and comparing a value of complexity counter with a threshold to determine the complexity value associated with the input signal.

2. The apparatus as recited in claim 1, wherein said measurement processor automatically compares the determined stability value with a threshold value to determine the quality of the input signal.

3. The apparatus as recited in claim 2, wherein said measurement processor assigns a weight associated with the input signal in response to the comparison between the stability value and the threshold value.

4. The apparatus as recited in claim 3, wherein said detector determines whether an input signal should be used in determining the at least one patient parameter using the assigned weight associated with the input signal.

5. The apparatus as recited in claim 1, wherein said detector simultaneously detects repetitious phenomena data on a plurality of input signals being received from a respective sensor and said measurement processor simultaneously determines the quality of said plurality of input signals.

6. The apparatus are recited in claim 5, wherein said detector generates patient parameter data from the input signals using the determined signal quality associated with each input signal by multiplying an amplitude average of the input signal by the stability value and a weight associated with the stability value for each input signal to obtain a weighted signal quality value for each signal, summing the weighted signal quality value for each input signal and dividing the sum of the weighted signal quality values for each input signal by a sum of the amplitude average of each input signal.

7. The apparatus as recited in claim 1, wherein the repetitious phenomena data is ECG data and the detector detects QRS complexes from the ECG data.

8. The apparatus as recited in claim 7, wherein the at least one feature of the repetitious phenomena data includes at least one of (a) a height of a QRS complex; (b) a width of a QRS complex; (c) a triangle area of a QRS complex; (d) a triangle area of an ST-segment; (e) a peak direction of a QRS complex; and (f) an RR interval between successive QRS complexes.

9. The apparatus as recited in claim 1, wherein said measurement processor assigns a weight associated with the input signal in response to determining the complexity value associated with the input signal and determines whether an input signal should be used in determining the at least one patient parameter based on the weight associated with the input signal.

10. The apparatus as recited in claim 9, wherein said detector determines the at least one patient parameter by selecting which input signals are to be used based on the stability value and complexity value.

11. The apparatus as recited in claim 9, wherein said detector generates patient parameter data from the input signals using the determined signal quality associated with each input signal by multiplying an amplitude average of each input signal by the stability value and a weight associated with the stability value for each input signal and the complexity value and a weight associated with the complexity value to obtain a weighed signal quality value for each signal, summing the weighted signal quality value for each input signal and dividing the sum of the weighted signal quality values for each input signal by a sum of the amplitude average of each input signal.

12. A method of determining a signal quality of an input signal representing a repetitious phenomena derived from at least one sensor connected to a patient comprising: receiving, by a detector, the input signal; determining, by the detector, data representing the repetitious phenomena from the input signal for use in determining at least one patient parameter; determining, by a measurement processor electrically coupled to the detector, a first signal quality value by identifying at least one feature of the repetitious phenomena data; comparing the at least one feature of a first set of the determined repetitious phenomena data with a second set of the determined repetitious phenomena data to determine a feature variability value; using the feature variability value to determine a stability value representative of the quality of the input signal, and further comprising the activity of measuring a second signal quality value associated with the input signal prior to the input signal being processed by the detector, wherein the activity of measuring further comprises evaluating a randomness of a finite sequence of data samples included in the input signal to determine a complexity value associated with the input signal and comparing the complexity value with a threshold to determine an amount of noise in the input signal the activity of evaluating includes converting the input signal into a binary signal; sequentially scanning the binary signal; incrementing a complexity counter by one upon detecting a change in a subsequence of consecutive characters in the binary signal; and comparing a value of complexity counter with a threshold to determine the complexity value associated with the input signal.

13. The method as recited in claim 12, further comprising the activity of automatically comparing the determined stability value with a threshold value to determine the quality of the input signal.

14. The method as recited in claim 13, further comprising the activity of assigning a weight associated with the input signal in response to the comparison between the stability value and the threshold value.

15. The method as recited in claim 14, further comprising the activity of determining whether an input signal should be used in determining the at least one patient parameter using the assigned weight associated with the input signal.

16. The method as recited in claim 12, further comprising the activity of simultaneously detecting repetitious phenomena data on a plurality of input signals being received from a respective sensor and measuring the quality of said plurality of input signals.

17. The method as recited in claim 16, further comprising the activity of generating, by the detector, patient parameter data from the input signals using the determined signal quality associated with each input signal by multiplying an amplitude average of the input signal by the stability value and a weight associated with the stability value for each input signal to obtain a weighed signal quality value for each signal, summing the weighted signal quality value for each input signal and dividing the sum of the weighted signal quality values for each input signal by a sum of the amplitude average of each input signal.

18. The method as recited in claim 12, wherein the repetitious phenomena data is ECG data and the activity of detecting detects QRS complexes from the ECG data.

19. The method as recited in claim 18, further comprising the activity of the at least one feature of the repetitious phenomena data includes at least one of (a) a height of a QRS complex; (b) a width of a QRS complex; (c) a triangle area of a QRS complex; (d) a triangle area of an ST-segment; (e) a peak direction of a QRS complex; and (f) an RR interval between successive QRS complexes.

20. The method as recited in claim 12, further comprising the activity of assigning a weight associated with the input signal in response to determining the complexity value associated with the input signal; and determining whether an input signal should be used in determining the at least one patient parameter based on the weight associated with the input signal.

21. The method as recited in claim 20, further comprising the activity of determining, by the detector, the at least one patient parameter by selecting which input signals are to be used based on the stability value and complexity value.

22. The method as recited in claim 21, further comprising the activity of generating patient parameter data from the input signals using the determined signal quality associated with each input signal by multiplying an amplitude average of each input signal by the stability value and a weight associated with the stability value for each input signal and the complexity value and a weight associated with the complexity value to obtain a weighed signal quality value for each signal, summing the weighted signal quality value for each input signal and dividing the sum of the weighted signal quality values for each input signal by a sum of the amplitude average of each input signal.

\* \* \* \* \*